(12) United States Patent
Horger et al.

(10) Patent No.: US 8,712,714 B2
(45) Date of Patent: Apr. 29, 2014

(54) MEASUREMENT PROTOCOL FOR A MEDICAL TECHNOLOGY APPARATUS

(75) Inventors: Wilhelm Horger, Schwaig (DE); Andre De Oliveira, Nuremberg (DE)

(73) Assignee: Siemens Aktiengesellschaft (DE)

( * ) Notice: Subject to any disclaimer, the term of this patent is extended or adjusted under 35 U.S.C. 154(b) by 604 days.

(21) Appl. No.: 12/971,338

(22) Filed: Dec. 17, 2010

(65) Prior Publication Data
US 2011/0153255 A1 Jun. 23, 2011

(30) Foreign Application Priority Data
Dec. 18, 2009 (DE) .......... 10 2009 054 990

(51) Int. Cl.
*G01C 19/00* (2013.01)
(52) U.S. Cl.
USPC .......... 702/104
(58) Field of Classification Search
USPC .......... 702/104
See application file for complete search history.

(56) References Cited

U.S. PATENT DOCUMENTS

| | | | |
|---|---|---|---|
| 7,218,113 B2 | 5/2007 | Feiweier et al. | |
| 7,372,270 B2 * | 5/2008 | Sung et al. .......... | 324/314 |
| 7,447,536 B2 | 11/2008 | Hill | |
| 2005/0038336 A1 * | 2/2005 | Nimsky .......... | 600/410 |
| 2008/0172249 A1 | 7/2008 | Glaser-Seidnitzer et al. | |

OTHER PUBLICATIONS

"Automatic Scan Prescription for Brain MRI," Itti et al., Magnetic Resonance in Medicine, vol. 45 (2001) pp. 485-494.
"Robust Anatomy Recognition for Automated MR Neuro Scan Planning," Young et al., Proc. Intl. Soc. Mag. Reson. Med. 14 (2006), p. 1588.
"Comparison of Manual and Automatic Section Positioning of Brain MR Images," Benner et al., Radiology, vol. 239 No. 1 (2006) pp. 246-254.
"Automated Spine Survey Iterative Scan Technique," Weiss et al., Radiology, vol. 239, No. 1 (2006) pp. 255-261.
"Automated Observer-independent Acquisition of Cardiac Short-Axis MR Images: A Pilot Study," Boudewijn et al., Radiology, vol. 221 (2001) pp. 537-542.
"Clinical Evaluation of Automated Scan Prescription of Knee MR Images," Lecouvet et al., Journal of Magnetic Resonance Imaging, vol. 29 (2009) pp. 141-145.

* cited by examiner

*Primary Examiner* — Aditya Bhat
(74) *Attorney, Agent, or Firm* — Schiff Hardin LLP

(57) ABSTRACT

In a method and a computer-readable storage medium to optimize protocol parameters for an MR measurement protocol, the user can configure conditions for selected physical parameters in advance. Moreover, it is possible to configure rules for these parameters and/or for the conditions. In a next step physical values regarding the selected parameters are measured. The measured values are then applied to the configured conditions and/or rules in order to optimize the protocol parameters.

15 Claims, 3 Drawing Sheets

MEASUREMENT PROTOCOL FOR A MEDICAL TECHNOLOGY APPARATUS

BACKGROUND OF THE INVENTION

1. Field of the Invention

The present invention concerns data processing and medical technology and in particular concerns the setup of imaging apparatuses, for example magnetic resonance tomography systems.

2. Description of the Prior Art

Within the scope of an examination with imaging apparatuses in clinical practice—for example for magnetic resonance tomography (MRT), computed tomography (CT), positron emission tomography (PET) or other nuclear medicine apparatuses—the necessity arises to adapt the protocol parameters of a measurement protocol to patient-specific values and to other examination variables. For example, specific measurement protocol parameters must be adapted to the respective lung retention volume or to EKG values of the patient. These values vary from case to case and can often only be registered immediately before the respective examination or measurement (data acquisition).

In the interim, in clinical practice a number of predefined measurement protocols have emerged as helpful measurement protocols. However, when these predefined measurement protocols must be adapted to specific variables and values, in known methods it is often the case that only suboptimal protocol settings are found, which leads to a lower image quality and ultimately to a reduced diagnostic value.

Different protocol parameters of a measurement protocol are defined depending on the type of the examined organ and on additional clinical and/or medical variables. Examples of such protocol parameters are the following variables: TE=echo time, TR=repetition time, FOV=field of view, slice thickness etc.

In order to optimize the determination of the measurement protocol parameters, it is known in the prior art to provide methods to automate MR measurement sequences. For example, an automated creation of MR measurement sequences for the examination of knee joints is tested in one study (see F. E. Lecouvet et al., "Clinical Evaluation of Automated Scan Prescription of Knee MR Images" in: Journal of Magnetic Resonance Imaging 29:141-145 (2009)). Further clinical studies are likewise concerned with an automated generation of an MR measurement protocol: T. Benner et al., "Comparison of Manual and Automatic Section Positioning of Brain MR Images" in "Radiology", Vol. 239: No. 1—April 2006 and K. L. Weiss et al., "Automated Spine Survey Iterative Scan Technique" in "Radiology", Vol. 239: No, 1—April 2006.

A common goal of the methods mentioned in detail in the preceding and other methods from the prior art is to achieve a measurement protocol can be automated.

However, it has proven to be a significant disadvantage that these known methods provide no opportunity for configuration on the part of the user. Rather, the user is directed to the predetermined values. However, an adaptation of an existing protocol to current values is in many cases necessary for clinical and/or medical reasons.

In the known methods from the prior art this problem was solved by requiring the operator of the MR scanner to determine patient-specific data (for example the air retention volume, the size of the patient, his position on the table, his heart rate etc.). The operator thereupon selects such an MR protocol that he or she deems to be best suited from a set of MR protocols. In a subsequent step, the operator must manually adapt specific protocol parameters, for example an acquisition time, to patient-specific values (for example to the lung retention volume or to the field of view) according to the patient's size. This method has proven to be both very time-consuming and extremely error-prone since the danger of incorrect inputs increases due to the manual influence.

It should be taken into account that the determination of a suitable measurement protocol with the respective protocol parameters is frequently a multidimensional problem. This is based on the fact that the determination of the protocol parameters is at least partially dependent on the protocol parameters themselves. In other words, the selection of a first protocol parameter can affect the determination of an additional protocol parameter.

SUMMARY OF THE INVENTION

An object of the present invention is to provide a way that allows the provision of measurement protocols can be improved and simplified. In particular, the process of the determination of the individual protocol parameters should be optimized and a configuration capability with regard to conditions and rules to be established should be achieved for the user.

This object is achieved by a method to optimize protocol parameters for a measurement protocol for a medical apparatus in accordance with the invention as well as a non-transitory computer-readable storage medium.

In the following the invention is described according to the method. Advantages, features and alternative embodiments are similarly applicable to the storage medium, which may be formed by software and/or hardware modules.

A computer-implemented method for optimization of protocol parameters for a measurement protocol for a medical technology apparatus, wherein the measurement protocol is determined by the protocol parameters, includes the following steps:

configure at least one condition for a physical parameter to determine the protocol parameters;

configure at least one rule to determine the protocol parameters, wherein the rules define specifications for different physical parameters;

register physical values regarding the physical parameters, wherein the registered (measured and/or imported) physical values comprise patient-related and biophysical values;

apply the registered physical values to the configured rules and/or to the configured condition;

automatic, computer-assisted optimization of the protocol parameters depending on the registered physical values that are applied, wherein the at least one condition, the rules and the physical values can be modified independent of one another.

It is taken into account that the biophysical values are registered via an additional, further measurement and are not related to the subject (organ) to be examined. The biophysical values comprise a lung retention volume, an EKG measurement and/or cardiac signals. These biophysical values do not concern geometric variables of the subject to be examined with the medical technology apparatus, for example the size of the subject. The biophysical values are normally completely decoupled from and independent of the subject to be examined (for example, the lung retention volume or the heart rate is independent of the subject "liver" that is to be examined). In a preferred embodiment of the invention, the biophysical value is the lung retention volume (thus the lung hold duration of the patient).

The following terminology are used herein with the following meanings.

The terms "optimization" and "optimize" comprehensively and generally refer to an automatic or computer-assisted calculation. This calculation is optimized using optimization criteria. A significant aspect of the present invention is that the optimization criteria are configurable. In particular, they can be adapted or configured by a user. However, via the configuration of conditions and/or rules the user can even establish the optimization criteria during the measurement. For example, the user can establish specific priorities according to which one protocol parameter is more important than another. In principle, the optimization can be of an optimization existing protocol parameters. It is likewise possible to determine protocol parameters for the first time, and thus determine them anew.

In a preferred embodiment, the present invention is designed for the optimization of protocol parameters for a measurement protocol for an MR apparatus. However, alternative embodiments seen here likewise provide measurement protocols for other medical technology apparatuses, for example for PET, CT and/or other radiological apparatuses.

"Configuring" means to provide a modification capability or an adjustment or adaptation capability on the part of the user. According to one significant aspect of the present invention, the possibility should be provided to the user to affect the determination of protocol parameters (and therefore to affect the measurement protocol as a whole) without, however, having to forego the advantage of automatically preconfigured measurement protocols. In other words, it should thus be made possible for the user to make patient-specific (and thus case-specific) adjustments that affect the measurement protocol. The user is advantageously assisted by the system in the configuration (of the condition and/or the rules). This typically ensues by providing a screen mask and/or a predetermined menu from which the user can then select specific menu offers. This markedly facilitates the operation of the method or system according to the invention.

According to one aspect of the invention at least one "condition" can be configured or defined. The condition concerns a protocol parameter. A condition can be configured or defined by a user. In one advantageous embodiment of the invention, the conditions can also be linked by Boolean conditions, for example instance in the manner of: Condition A AND Condition B or NEGATION (Condition C). In principle, the conditions respectively refer to physical parameters that cannot by defined automatically in advance of a measurement. The physical parameters are, for example, patient-related parameters or measurement-specific parameters apparatus apparatus-specific parameters, thus generally parameters that are case-specific and cannot be established in advance.

According to a preferred embodiment, it is cumulatively or alternatively possible to configure "rules". However, this is an optional feature, such that no rules or only one rule can be configured. Moreover, in an alternative embodiment of the invention it can also be reasonable to configure only at least one rule and no conditions. The rules are definitions of the type "IF <Condition> THEN <Action>" or, respectively, "DO <Action> WHILE <Condition> is fulfilled/not fulfilled". Multiple conditions can normally be combined, for instance in the manner of: "IF Value W1 is in the range a through 2 AND IF Value W2 is below Threshold S1 THEN Protocol Parameter P1:=X". With the rules the user can thus establish which actions should be executed with regard to the protocol parameters under specific conditions, wherein the conditions concern recorded (for example measured and/or imported) values regarding the physical parameters, and wherein the action is related to the protocol parameters.

A two-fold configuration capability is therefore provided. Depending on which physical parameters are defined in the conditions and/or in the rules, according to the invention the respective physical values are measured and/or imported in a subsequent method step (which normally is executed immediately before the measurement). In this context it is noted that the terms "parameter" and "value" are to be understood in the typical, mathematical sense. The term "parameter" should thereby be understood in the sense of a variable or a placeholder while a value is a concretely recorded (measured or imported) variable of the respective parameter. For example, a concrete value for the parameter "patient size" can be the specification "1.85"; a physical value for the parameter "field of view (FOV)" could be, for example, the specification "220-240". The concrete, physical values are normally not to be determined in advance and are dependent on the respective medical case. They can depend on the patient, on the type of examination, on the time period of the examination, on the examination modal, on the person to be examined and/or on other variables. According to the invention, different manners of how the physical values are recorded are provided. The values are advantageously measured (this can ensue immediately before the MR examination or have already taken place at an earlier point in time), and/or the physical values can also be imported via a corresponding interface.

For example, it is possible that the physical values are already known from prior examinations and do not need to be measured (and thus repeated) again. Moreover, it is possible that the physical values are input manually, for example by the examiner or even directly by the patient. For those skilled in the art it is clear that further registration modalities lie within the scope of the invention in addition to the possibilities mentioned in the preceding for automatic or manual registration of physical values.

Within the scope of this invention a differentiation is made between a "protocol parameter" and a "physical parameter." The first term "protocol parameter" concerns the parameters of the measurement protocol to be optimized (for example TR, TE, slice thickness etc.) while the second term concerns parameters that, specific to situation and context, are related to physical or technical variables of the system, but that have an influence on the measurement protocol with its protocol parameters (for example organ size, patient size, position of the patient, etc.).

As soon as the concrete physical values regarding the relevant physical parameters have been registered, it is possible to apply the configured conditions and/or the configured rules with the registered physical values. In the mathematical sense, this procedure corresponds to the insertion of concrete measurement values into an equation with variables. This is a calculation process that is executed wholly automatically, implemented by computer. In the "application" it is thus examined which conditions and/or rules are now satisfied for the concretely registered physical values and which are not. The configured actions or, respectively, sequences are executed accordingly. These relate to the determination of the protocol parameters.

In a last step it is thus possible to optimize the current REAL protocol parameters using the configured rules and/or conditions for the concretely registered physical values with the optimized (i.e. calculated) TARGET protocol parameters. The optimization advantageously ensues wholly automatically. In other words, no additional user input is necessary. An access to the existing protocol data set is provided for this. However, in an advantageous development of the invention it is provided that a confirmation by the user is requested given the execution of an optimized measurement protocol sequence. This occurs in order to increase the safety and to avoid an unwanted overwriting of a measurement protocol sequence. However, it can be preset that the user confirmation is only required in the event that an existing measurement protocol has actually been modified or optimized.

According to a further aspect of the invention, dependencies between the protocol parameters can be modeled and calculated. This is possible in that the user configures the conditions and/or the rules accordingly. It is thus possible for the determination of a first protocol parameter to be defined depending on the determination of a further protocol parameter by means of the configuration of a rule. This presumes a time sequence in the determination of different protocol parameters in the event that an additional protocol parameter should be determined depending on preceding protocol parameters. Other dependencies can likewise be mapped by the configuration of corresponding rules. For example, it is also possible to configure specifications that are dependent on other parameters, for example depending on already-executed prior examinations, parallel examinations or planned future examinations.

According to a further aspect of the invention, the registered physical values (which can be measured and/or imported, for example) are patient-related, biophysical and/or measurement-specific values. The values can in principle be imported automatically via an interface, for example from a Radiology Information System (RIS system) or from a Picture Archiving and Communication System (PACS system). Moreover, it is also possible to input the values manually via a provided user interface. The registration or the input or the importation of the values advantageously takes place immediately before the measurement. Alternatively, it is also possible to have already registered the values in a preparation phase. It is likewise possible to also register the values in parallel and (so to speak) simultaneously with the MR examination. For example, this is necessary when EKG signals or cardiac signals must be registered to determine protocol parameters during the MR examination. In addition to the patient-related, biophysical or measurement-related values, the values can also relate to other physical variables and/or apparatus-related variables. Due to the number of parameters to be configured, according to the invention a high variability and flexibility can advantageously be achieved in the optimization.

According to a further aspect of the invention it is provided that, given the application of the registered physical values to the configured rules and/or to the configured condition, which configured condition and/or which configured rule for the respective registered physical value is satisfied and which is not is analyzed. With this it is established which action should be executed in light of the protocol parameters. In a preferred embodiment the term "action" refers to a selection of a concrete measurement protocol parameter and therefore to its optimized determination.

The configuration of the rules and/or the configuration of the at least one condition is advantageously conducted by the user of the system. Configuration individual to the user can therefore be conducted. The optimization process can thus be designed specifically from use case to use case. However, it is likewise possible that the configuration is executed according to predefined workflows in the event that no case-specific adaptation and optimization is necessary.

In a preferred embodiment of the invention the method can be subdivided into two time segments: on the one hand a configuration phase is provided that is followed on the other hand by a preparation phase to prepare the actual measurement. These two phases are typically independent of one another so that the preparation phase can be started at an arbitrary point in time (and independent of the configuration phase). However, the preparation phase to prepare the measurement is typically executed after the conclusion of the configuration phase. However, it is also possible that the two time phases overlap. The method steps of the configuration (of the at least one condition on the one hand and of the at least one rule on the other hand) typically take place in the configuration phase. In the preparation phase the registered (measured and/or imported) physical values are applied to the configured rules and/or conditions and the automatic optimization of the protocol parameters ensues. Alternatively, it is also possible that only the optimization of the protocol parameters is executed in the preparation phase while the step of the application is still associated with the configuration phase.

One significant feature of the solution according to the invention is the configuration capability on the part of the user, which does not need to be patient-specific and also can be executed during a setup for the measurement protocol. It is likewise possible that the optimization process can also be executed during a currently running MR measurement in the event that the user starts an optimization routine. If the optimization routine then has the result that the current protocol parameter should be replaced with optimized protocol parameters, this can also be executed online and, so to speak, via a corresponding user confirmation during a measurement process. An optimization on-the-fly can therefore be executed.

In a preferred embodiment of the invention, the user can select the physical parameters from a proposed set of physical parameters that are relevant to his or her respective use case. In other words, the method can include an additional method step:

select relevant physical parameters to determine the protocol parameters for which conditions and/or rules can then (later) be configured and values can be registered.

The optimization method therefore can be executed even more efficiently in that the primary attention is placed exclusively on relevant physical parameters. For example, given very short, less complex MR measurements it is thus not necessary to register physiological parameters of the patient (for example the heart beat, the lung retention volume, blood values or the like) in the event that the knee should be examined (for example). The optimization method can therefore be abbreviated and the user does not have to click through menus that pertain to irrelevant parameters.

According to a further aspect, the optimization method is executed by an optimization module (which can be a software or hardware module, for example) that advantageously runs on the MR scanner. The optimization module interacts with additional devices of the radiology system, for example with an image reconstruction computer, a memory (in particular for protocol data sets and protocol-specific data), an information system, etc.

The configuration is advantageously executed via a prepared user interface. A script is thereby generated that is subsequently interpreted and executed on the optimization module. It is thereby advantageously possible to store the configured rules and/or the configured conditions in order to also make these settings available for subsequent optimization methods.

In complex medical cases it can be necessary that certain rules and/or certain conditions can be configured only in stages, and thus only under specific conditions. For example, the configuration of a rule and/or a condition can be dependent on the registration of a physical value. Moreover, the configuration can also be dependent on a preceding configuration. In order to also cover these use cases, in a further embodiment of the invention it is also provided that the optimization method is applied iteratively.

A significant advantage of the solution according to the invention is apparent in that each user has different configuration capabilities, such that user A can make use of one configuration a while an additional user B can make use of an additional configuration b that is tailored to the user B. Each user thus can work with a protocol optimization that is tailored to that user. Furthermore, it is possible to map individual, user-specific requirements or, respectively, to consider them in the optimization process. Different priorities can be set via the configuration possibilities, such that it is possible (for example) to allow the resolution a higher priority than the signal-to-noise ratio.

A significant additional advantage of the invention is also that the optimization of the protocol can be executed wholly automatically. Moreover, the optimization can also be executed at run time—thus during an MR examination—as soon as a configuration has been executed. It is thus also possible for a configuration (thus all configurations executed within the scope of the optimization according to the invention, for example the rules, conditions, specifications that are advantageously stored in a configuration memory) to be used repeatedly for different MR examinations. This contributes to the marked efficiency increase in the execution of medical examinations or in the adjustments of the respective apparatuses.

An additional advantage is also that the number of protocols to be generated can be markedly reduced since it is no longer necessary to generate different protocols for every application case. One and the same protocol can be automatically adapted to different application situations and even to different patient-specific situations.

It has also proven to be advantageous that the time duration to execute the examination can be markedly reduced since the optimization can be executed automatically, which accelerates the workflow as a whole.

An additional advantage is in the increased image quality. Errors that are caused by incorrect, manual inputs can be avoided via the wholly automatic protocol optimization or protocol adaptation. The improved optimization process also contributes to avoiding unwanted image effects, for example movement artifacts or suboptimal image contrasts. By providing different configuration capabilities, an adaptation of variation strategies at a hierarchically superordinate level is possible; the respective adaptations are thereby executed automatically.

The optimization process is self-executing. This means that the system automatically checks whether the configured conditions and/or the configured rules for the registered (measured or input) physical values are satisfied and whether modifications to the protocol parameters are therefore to be executed. In the event that modifications are necessary, these are executed automatically. In the event that they are not, an optimized measurement protocol already exists; otherwise, the current (REAL) parameters are replaced with the optimized (DESIRED) parameters.

The optimization method described according to the invention can be used to implement a medical technology examination with a medical technology apparatus (advantageously an MR apparatus). During the execution of the MR measurement the measurement protocol is optimized at run time using the optimization method by, if necessary, replacing the current real protocol parameters with calculated, optimized target protocol parameters.

The present invention also encompasses a non-transitory computer-readable storage medium that includes a configuration module, a registration module and a calculation module. The modules can be connected to the MR scanner as separate components via corresponding interfaces. It is likewise possible to implement the modules directly in the MR scanner. It is also possible to provide these modules as a computer program product that can be retrieved from a server via a web-based interface. The individual modules can likewise also be implemented at different medical technology apparatuses, such that individual segments of the method described in the preceding or individual modules of the system can be executed as a commercial unit while the remaining segments or modules can be executed in a different unit.

DESCRIPTION OF THE PREFERRED EMBODIMENTS

In the following the invention is described using exemplary embodiments that lie in the field of medical technology, in particular in the field of radiology. Additional application possibilities lie in the optimization of CT, US, PET or other measurement protocols.

Figure 1:
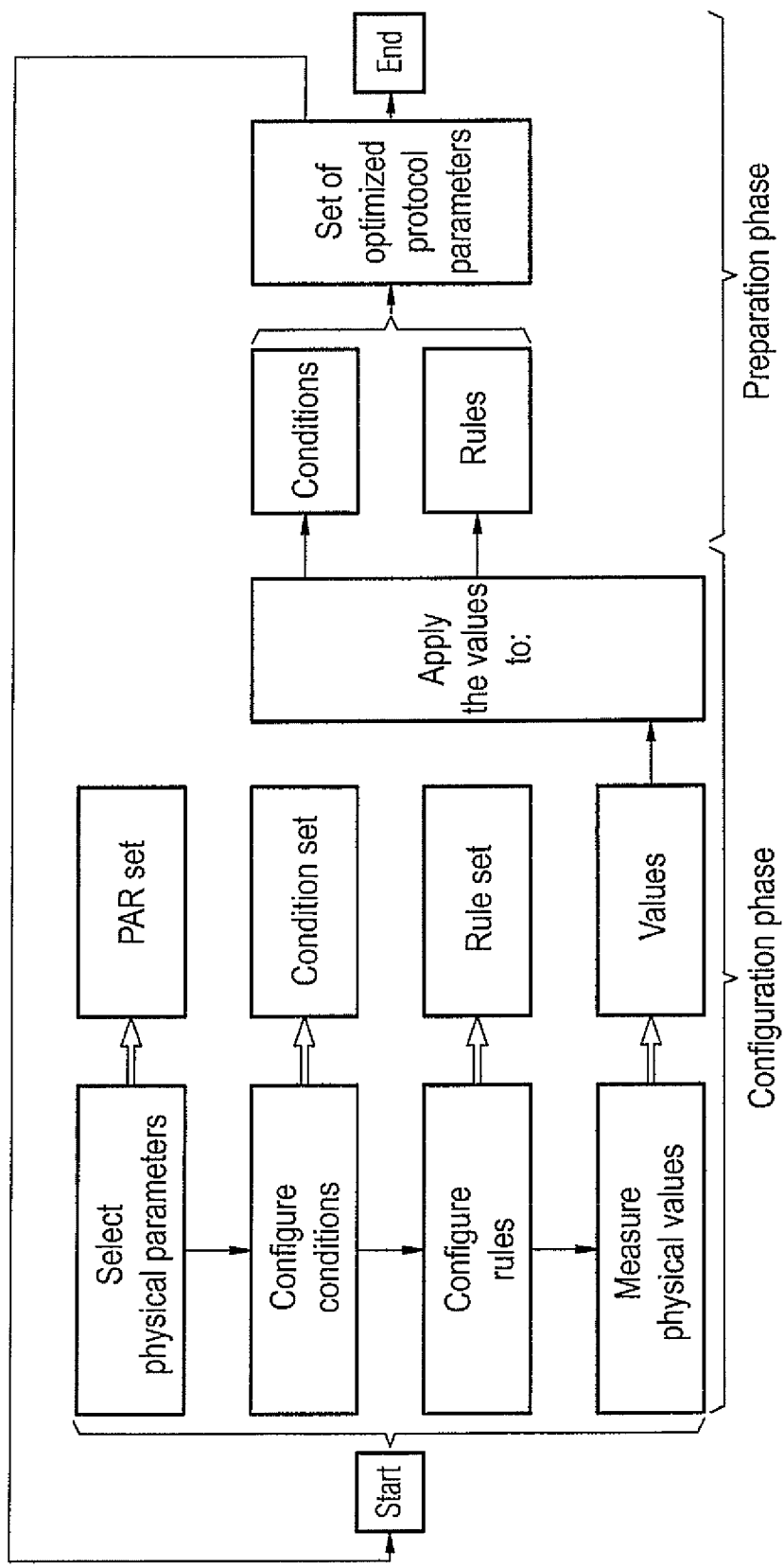
FIG. 1 is a schematic overview of a workflow according to the invention according to a preferred embodiment.

In one schematic representation FIG. 1 shows the actions executed according to the invention with their respective results. At the end (shown on the right side in FIG. 1) a set of optimized protocol parameters is obtained or emitted as an output. For this purpose, it is necessary to execute a series of adjustments in advance that are shown in FIG. 1. The order of the steps can be varied if necessary. According to a preferred embodiment physical parameters that are relevant to the current cases or MR examinations are initially determined in a preparation step. Conditions are thereupon configured for the selected physical parameters. These conditions can pertain to region specifications, comparisons with thresholds, comparisons with normal values or other reference values. They can be implemented in the form of "IF→THEN" or equivalently with "WHILE→DO". If a complex optimization task is dealt with, it is thus possible to provide a further configuration capability in addition to the configuration of the conditions; however, this is not absolutely necessary and is merely optional. This additional configuration capability relates to the configuration of rules. Multiple conditions can be combined in one rule, for instance in the manner of "IF Value W1 in Range [a, . . . , d] AND IF Value W2 below threshold for normal value S1 THEN set Protocol Parameter P1:=X". This rule thus refers to two physical values or, respectively, to two parameters W1 and W2. Those skilled in the art will understand that arbitrary links can be defined between the individual conditions. Moreover, rules can also be linked with one another. With these configuration capabilities (which are not provided in the previous methods in the prior art) it is possible to automate a protocol optimization and to markedly simplify it in that optimization criteria do not need to be continuously input repeatedly but rather in that rules can be defined for these that are automatically applied in a protocol optimization.

Furthermore, it is possible to define priorities for the use case here and, for example, to process specific physical parameters with higher priority than other parameters. It is likewise possible to map dependencies between the determination of the protocol parameters.

The dependencies in the determination or optimization of protocol parameters are explained in the following example. For example, if an axial measurement of a liver should be executed in which the patient must hold his breath in order to not adulterate the image (for example with a VIBE sequence), a typical measurement protocol will be started with a coverage of 72 slices with 3 mm slice thickness respectively. With these protocol parameter settings a standard liver is covered completely and can be measured during a breath-hold of the patient of 20 seconds. However, in the event that these parameters cannot be complied with—for example because the patient can hold his breath for only a shorter time period (for example 15 seconds) and/or because the liver of the patient is enlarged—other protocol parameters must be selected. An optimization is thus necessary since a larger coverage is necessary. For example, the number of slices must be increased from 72 to 80. Moreover, an adaptation of the physical parameters must ensue in order to change the "PhasePartialFourier" data set from 8/8 to 6/8 (for example) in order to again obtain a measurement time that lies within the time period in which the patient can hold his breath (15 seconds in the preceding example). This example should thus clarify that a modification of physical parameters (here of patient-related parameters, for example size of the liver, time duration of the breath-hold etc.) also make an optimization of protocol parameters necessary.

Moreover, it is possible that a modification, adaptation or optimization of a protocol parameter also entails a modification of other protocol parameters. This iterative execution of the method should be represented in FIG. 1 by the arrow that—starting from the result, namely the set of optimized protocol parameters—again points to the left side, and therefore to the beginning of the method.

In the aforementioned example the selected physical parameters are:
1. breath-hold time duration and
2. liver size.

Via the configuration of the conditions and the rules it is possible to define the number of necessary slices and the respective slice thickness depending on the parameters mentioned in the preceding.

The method steps necessary at this point in time—thus the selection of physical parameters, the configuration of conditions for these physical parameter and the configuration of rules for the physical parameters—can be executed at an arbitrary point in time in advance of an examination. This is typically executed in a configuration phase that, in principle, can be executed independent of the actual executed MR measurement and chronologically precedes it. A further step is associated with the configuration phase in FIG. 1. This relates to the measurement of the physical values for the selected physical parameters. This step does not necessarily have to be executed in the configuration phase; rather, it can also ensue immediately before the measurement and thus can also be associated with the preparation phase.

In FIG. 1 which result the method steps shown in the first column have is shown in the second column. The selection of physical parameters thus leads to a set of parameters, the configuration of conditions leads to a condition set, the configuration of rules leads to a rule set and the measurement of physical values regarding the selected physical values leads to a set of values. These are advantageously stored in separate files so that they can also be modified independent of one another. Moreover, in a further embodiment these sets or files can also be accessed by external instances. As soon as a parameter set, and a condition set have been defined, the configuration phase can be terminated. The actual optimization can then be executed fully automatically at an arbitrary, later point in time in that the concrete values regarding the physical parameters are measured. The term "measure" here is to be understood comprehensively in the sense of a "registration". It should therefore be noted that the values are registered by an additional, further measurement (for example by the MR scanner itself or by other apparatuses, for example EKG, blood pressure measurement apparatuses etc.). It is likewise possible that the values are imported from other computer-assisted units via an interface. In the event that the patient has already been examined once, the patient size and the patient weight (for example) can be retrieved or imported from a memory of another module (RIS, PACS or the like). It is naturally also possible that the user and/or the patient here manually inputs specific inputs [sic] with regard to the values.

After the values have been registered it is possible to apply these values to the configured conditions and/or to the configured rules. At this point it is again noted that the configuration of rules is not absolutely necessary. The configuration of rules is provided only for complex optimization cases in which priorities should be defined, for example. Simple optimization tasks merely provide a configuration of conditions.

In FIG. 1 it is shown in the third column that the registered (measured, manually input or registered in another manner) values are applied to the configured conditions and/or rules. This application has the result that the protocol parameters defined in the conditions and/or rules are possibly modified. The modified protocol parameters are then optimized for the respective use case (with the concrete physical values that, so to speak, are "used" in the configured conditions and/or rules).

However, the invention can be implemented not only as a pure software solution in a computer program product; rather, it is also possible to provide a hardware implementation. A computer-assisted system thereby has a configuration module K that is fashioned to configure at least one condition for selected physical parameters and that furthermore can optionally be fashioned to configure at least one rule. Furthermore, the system comprises a registration module E that is fashioned to measure and/or import and/or for manual input of physical values regarding the selected physical parameters. The registration module E can possess arbitrary registration modalities and implement both an automatic and a manual registration. Moreover, the system comprises a calculation module B that is fashioned to apply physical values registered by means of the registration module E to the configured rules and/or to the configured condition. Furthermore, the calculation module B is fashioned to automatically optimize the protocol parameter. The optimization thereby ensues depending on the application of the registered, physical values to the configured rules and/or conditions.

Figure 2:
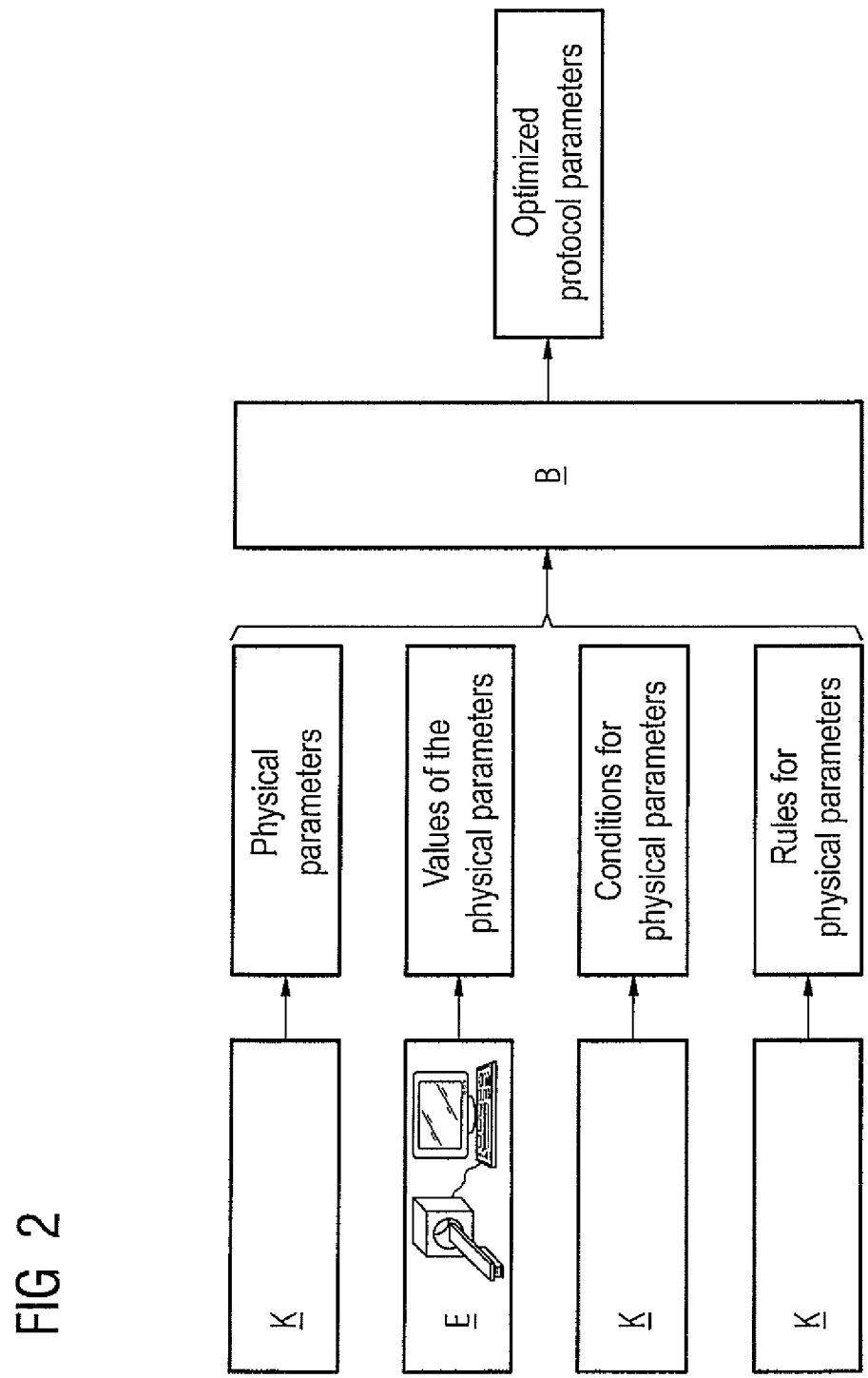
FIG. 2 is a schematic input/output representation of the method according to a preferred embodiment.

In FIG. 2 the configuration module K and the registration module E are depicted on the left side. The arrows emanating from the modules (which point to the right in FIG. 2) should mark the results of the respective modules. In the configuration module K the relevant physical parameters are selected. Moreover, in the configuration module K the conditions for the (selected) physical parameters are configured. The rules for the (selected physical parameters) are likewise configured in the configuration module K. The concrete values regarding the selected physical parameters can be registered to the registration module E. The registration module can thereby also be integrated into the MR scanner, thus into the medical technology apparatus. All of the variables (physical parameters, values, conditions, rules) cited in the preceding are supplied to a calculation module B as input variables (input). The calculation module serves to calculate or, respectively, to optimize the protocol parameters.

In advantageous developments of the invention the calculation module B can be fashioned with additional auxiliary modules. These modules can serve to automatically correct errors (for example input errors) or to provide a notification to the user.

Figure 3:
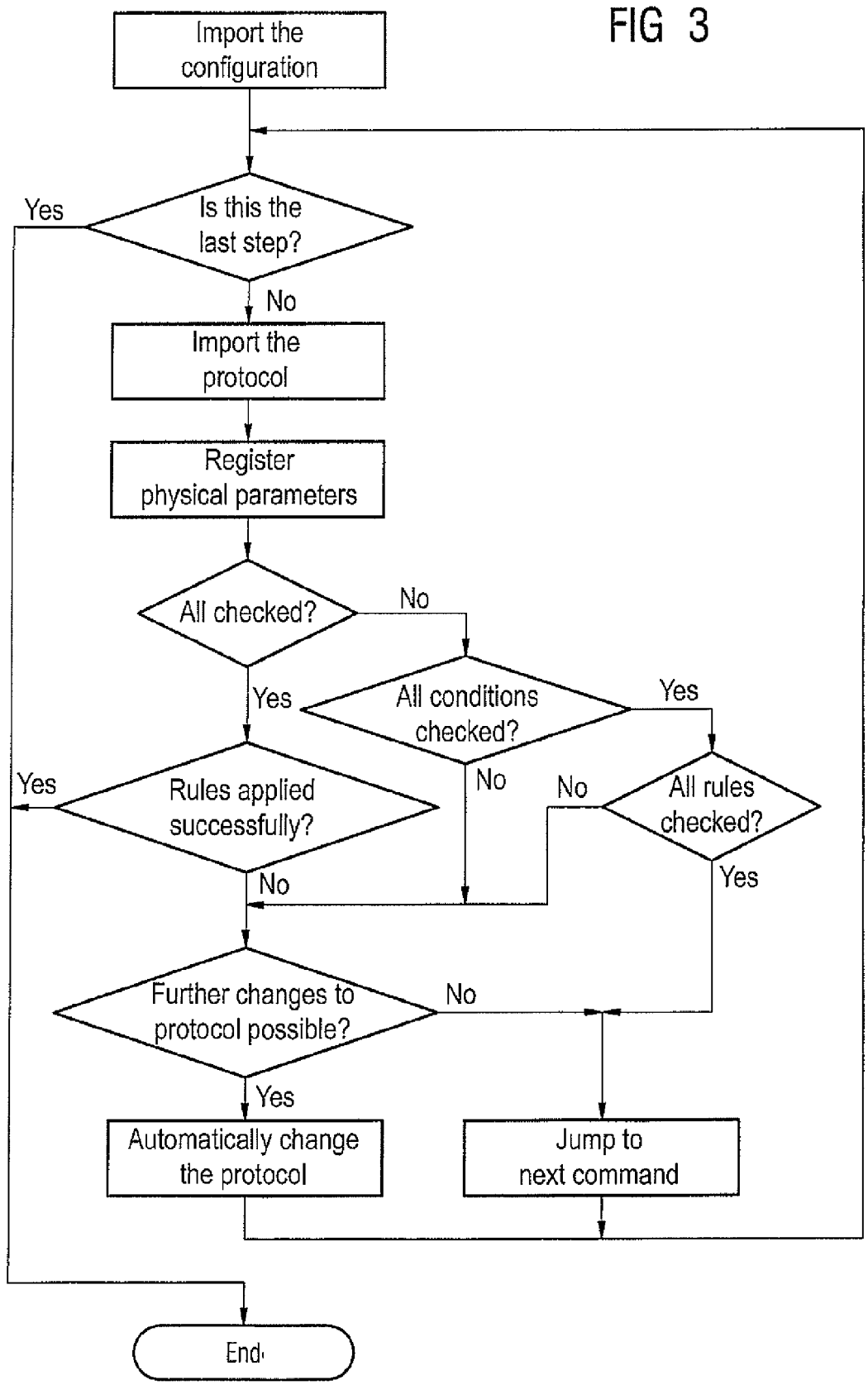
FIG. 3 is a workflow diagram according to a preferred embodiment of the invention.

In FIG. 3 a workflow diagram is shown that should explain in detail a typical workflow according to a preferred embodiment. In a first step the configurations are thereby imported. In a simple embodiment only conditions are thereby configured. Both [sic] only one condition can hereby be defined. However, normally a number of conditions are configured here. Rules can optionally be additionally configured, wherein the rules define specifications for different physical parameters.

A check is implemented as to whether this is the last step of the method. If it is not, the current protocol is important and the physical parameters are registered. This step comprises both the selection of relevant physical parameters and the registration (via measurement and/or via importation) of the concrete physical values regarding the physical parameters.

In a following step it is checked whether all values and/or parameters are examined. If this is not the case it is checked whether all conditions are checked. If yes it is examined whether all rules have also be checked. If yes, the workflow jumps to the next command.

In the event that not all conditions or not all rules have been checked it is examined whether changes to the protocol are still possible. In the event that changes are no longer possible, the workflow likewise jumps to the next command. In the event that further changes are possible, an automatic modification or, respectively, optimization of the protocol is executed.

After all specifications have been checked it is examined whether all rules, conditions and other specifications have been successfully applied. If this can be answered affirmatively, the method ends. Otherwise it is examined whether additional changes to the protocol are possible and the workflow proceeds as has already been explained in the preceding.

In the following, additional information regarding the configuration capability of the conditions should be provided again. Limits that the specific protocol parameters must comply with can be defined in the conditions.

The rules establish which protocol parameters are to be modified in which order. The protocol change or protocol optimization is advantageously blocked and can thus not be executed while the MR protocol itself is being executed. However, since this occurs very quickly (<0.5 sec) due to the optimized algorithm for the optimization process, the user also does not need to put up with a long wait time. For example, a rule could read:

Modify (reset, increase, decrease) [Protocol Parameter] until [Value] with a step size of [Value] if [Condition] is not satisfied."

In the MR examination of the liver of a patient it is normally necessary to conduct relatively complex protocol manipulations in order to be able to adjust optimal settings in relation to the current patient position, the patient size and/or in relation to his lung retention volume. A predetermined MR protocol is thereby typically started that is optimized according to the invention. The slices are initially positioned and the image section (field of view, FOV) is thereupon considered with an acceptable signal-to-noise ratio (signal-to-noise ratio). Ultimately the acquisition duration is optimized for the respective patient in order to generate the best image quality.

In the preceding example the respective settings (for example pertaining to FOV, SNR, organ size etc.) can also be populated with specific tolerance values.

For example, in cardiological examinations the acquisition time duration is dependent on the lung retention volume. In particular, the acquisition duration must be smaller than the lung retention volume in order to be able to ensure a sufficient image quality. The acquisition time duration is still additionally dependent on other parameters, for example on the organ size and—in cardiological examinations—on the length of the RR interval (RR here stands for the time interval between the beginning of a QRS complex of an electrocardiogram the beginning of the following QRS complex) that affects the phase coding steps. In such cases more complex rules must thus be configured in order to be able to taken into account the dependencies between the protocol parameters.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computerized method for optimization of protocol parameters for a data acquisition protocol that operates a medical data acquisition apparatus, said method comprising the steps of:

in a computerized processor, designating a protocol for operating a medical data acquisition apparatus in order to execute a data acquisition procedure according to said protocol, to obtain medical data from a patient, said protocol comprising a plurality of protocol parameters that respectively define physical or technical variables of the apparatus that must each be set to a parameter value;

via said processor, defining a condition for at least one of said protocol parameters that is dependent on said data acquisition procedure;

via said processor, configuring at least one rule that interrelates at least two of said protocol parameters, said at least one rule causing modification of one of said at least two of said protocol parameters when another of said at least two of said protocol parameters changes;

entering a patient-specific, biophysical value of said patient into said processor that describes internal anatomy or physiology of the patient;

in said processor, automatically optimizing said protocol parameters, dependent on said biophysical value, by modifying at least one of said defined condition and said at least one rule independently of each other, to obtain an optimized protocol comprising optimized protocol parameters; and making said optimized protocol available at an output of the processor in an electronic form configured to operate said medical data acquisition apparatus according to said optimized protocol.

2. A method as claimed in claim 1 comprising successively determining said protocol parameters by iteratively executing said steps, with at least some of said protocol parameters being determined dependent on previously-determined protocol parameters.

3. A method as claimed in claim 1 comprising entering lung retention volume into said processor as the biophysical value.

4. A method as claimed in claim 1 comprising entering at least one value into said processor selected from the group consisting of heart rate and ECG-based values, as said biophysical value.

5. A method as claimed in claim 1 comprising optimizing said protocol parameters using said configured rules and said at least one condition using optimization criteria compiled for a group of patients.

6. A method as claimed in claim 1 comprising also entering physical values into said processor representing measurement specific values of the data acquisition, and automatically entering the biophysical values into the computerized processor via an interface or a manual input, and wherein the measurement specific values comprise physical variables or apparatus-related variables.

7. A method as claimed in claim 1 comprising requiring confirmation of an operator of the data acquisition apparatus before implementing said data acquisition according to said optimized protocol.

8. A method as claimed in claim 1 comprising optimized said protocol by applying the biophysical value entered into the processor to the at least one configured rule and the condition to determine how the protocol parameters must be optimized for the biophysical value given the defined condition and the at least one configured rule.

9. A method as claimed in claim 1 comprising manually configuring said at least one rule and manually defining said at least one condition in a manner customized for an operator of the medical technology apparatus.

10. A method as claimed in claim 1 comprising configuring the rules and the at least one condition in a configuration phase, and registering the physical values, applying the registered physical values, and optimizing the protocol parameters in a preparation phase.

11. A method as claimed in claim 1 comprising configuring said at least one rule and defining said at least one condition by manual interaction with a predetermined screen mask for a menu displayed at a display screen of the processor.

12. A method as claimed in claim 1 comprising, in said processor, designating at least one of said protocol parameters as a precluded parameter and automatically precluding said precluded parameter from being among said protocol parameters for which said condition is defined.

13. A method as claimed in claim 12 comprising designating said precluded parameter to be a parameter that will be otherwise accounted for in said protocol with said data acquisition apparatus.

14. A method as claimed in claim 1 comprising manually selecting at least some of said protocol parameters.

15. A non-transitory, computer-readable data storage medium encoded with programming instructions said data storage medium being loaded into a computerized processor and said programming instructions causing said processor to:

designate a protocol for operating a medical data acquisition apparatus in order to execute a data acquisition procedure according to said protocol, to obtain medical data from a patient, said protocol comprising a plurality of protocol parameters that respectively define physical or technical variables of the apparatus that must each be set to a parameter value;

define a condition for at least one of said protocol parameters that is dependent on said data acquisition procedure;

configure at least one rule that interrelates at least two of said protocol parameters, said at least one rule causing modification of one of said at least two of said protocol parameters when another of said at least two of said protocol parameters changes;

receive a patient-specific, biophysical value of said patient into said processor that describes internal anatomy or physiology of the patient;

automatically optimize said protocol parameters, dependent on said biophysical value, by modifying at least one of said defined condition and said at least one rule independently of each other, to obtain an optimized protocol comprising optimized protocol parameters; and make said optimized protocol available at an output of the processor in an electronic form configured to operate said medical data acquisition apparatus according to said optimized protocol.

* * * * *